US00PP36173P2

(12) United States Plant Patent
Brand et al.

(10) Patent No.: US PP36,173 P2
(45) Date of Patent: Oct. 1, 2024

(54) ***PRUNUS* PLANT NAMED 'UCONNPCSDR'**

(50) Latin Name: *Prunus cistena*
Varietal Denomination: UCONNPCSDR

(71) Applicant: University of Connecticut, Farmington, CT (US)

(72) Inventors: Mark Henry Brand, Willington, CT (US); Bryan Allan Connolly, Mansfield Center, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 18/541,431

(22) Filed: Dec. 15, 2023

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226, 182
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Prunus* plant named 'UCONNPCSDR' is disclosed, characterized by a low, compact, mounded plant habit, and dusky pink buds opening to white flowers. Foliage is red-purple-flushed in spring, to burgundy-colored in summer. The new cultivar is a *Prunus*, suitable for ornamental garden purposes.

2 Drawing Sheets

STATEMENT REGARDING FEDERALLY-SPONSORED RESEARCH AND DEVELOPMENT

Figure 1:
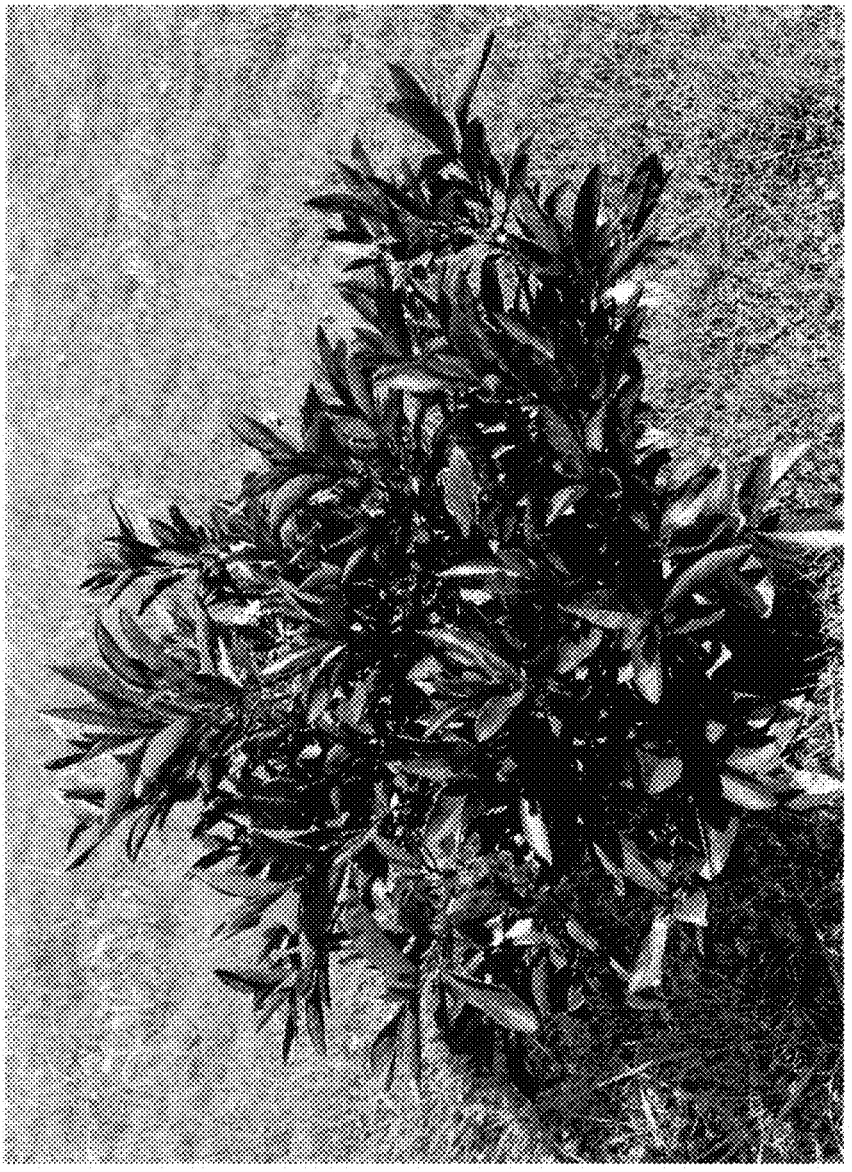

This invention was made with U.S. Government support under NI23HFPXXXXXG049 awarded by the National Institute of Food and Agriculture. The U.S. Government has certain rights in the invention.

Latin name of the genus and species: *Prunus*x*cistena*.
Cultivar denomination: 'UCONNPCSDR'.

BACKGROUND OF THE INVENTION

The new cultivar is a product of breeding program with the intent to produce compact, low-growing *Prunus* varieties. The new cultivar is the result of a crossing made in Storrs, Connecticut in May of 2013. The seed parent is an unnamed, unpatented, internally selected plant, *Prunus pumila* var. *depressa* . The pollen parent is the unpatented *Prunus x cerasifera* var. *atropurpurea* 'Thundercloud'. The new cultivar was selected in May of 2018 at the same nursery in Storrs, Connecticut.

'UCONNPCSDR' was first propagated by softwood cuttings at the same nursery in Storrs, Connecticut in June of 2018. Subsequent generations have been reproduced and have shown that the unique features of this cultivar are stable and reproduced true to type.

Date of first public disclosure was Jun. 27, 2023, in the United States. This disclosure was made directly by the inventor or one who obtained the claimed invention directly or indirectly from the inventor. This disclosure and all public disclosures made between Jun. 27, 2023, and the filing of this application fall within the exception allowed under 102(b)(1).

SUMMARY OF THE INVENTION

The cultivar 'UCONNPCSDR' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'UCONNPCSDR'. These characteristics in combination distinguish 'UCONNPCSDR' as a new and distinct *Prunus* cultivar:

1. Low, mounded habit; significantly smaller size compared to existing *Prunus* x *cistena* currently on the markey known to the Inventors.
2. Red-purple spring flush and burgundy-colored summer foliage.
3. Dusky pink buds opening to white flowers.
4. Easy propagation and container production.

PARENT COMPARISONS

Plants of the new cultivar 'UCONNPCSDR' are similar to plants of the seed parent in most horticultural characteristics, however, the new cultivar differs in the following:

1. Plants of the new cultivar are compact, mounded, and low-growing, while plants of the seed parent are prostrate and sprawling.

Plants of the new cultivar 'UCONNPCSDR' are similar to plants of the pollen parent in most horticultural characteristics, however, the new cultivar differs in the following:

1. Plants of the new cultivar are compact, mounded, and low-growing, while plants of the pollen parent are upright.
2. Plants of the new cultivar are less floriferous than plants of the pollen parent.

COMMERCIAL COMPARISON

'UCONNPCSDR' can be compared to the unnamed, unpatented commercial variety of *Prunus*x*cistena* found in the industry and sold as Purple Leaf Sand Cherry. Plants of the new cultivar 'UCONNPCSDR' are similar to this comparator in most horticultural characteristics, however, plants of the new cultivar 'UCONNPCSDR' differ in the following:

1. Plants of the new cultivar have a smaller mature size than plants of this comparator.

BRIEF DESCRIPTION OF THE PHOTOGRAPHS

The accompanying photograph in FIG. 1 illustrates in full color a typical plant of 'UCONNPCSDR' grown outdoors in Grand Haven, Michigan.

Figure 2:
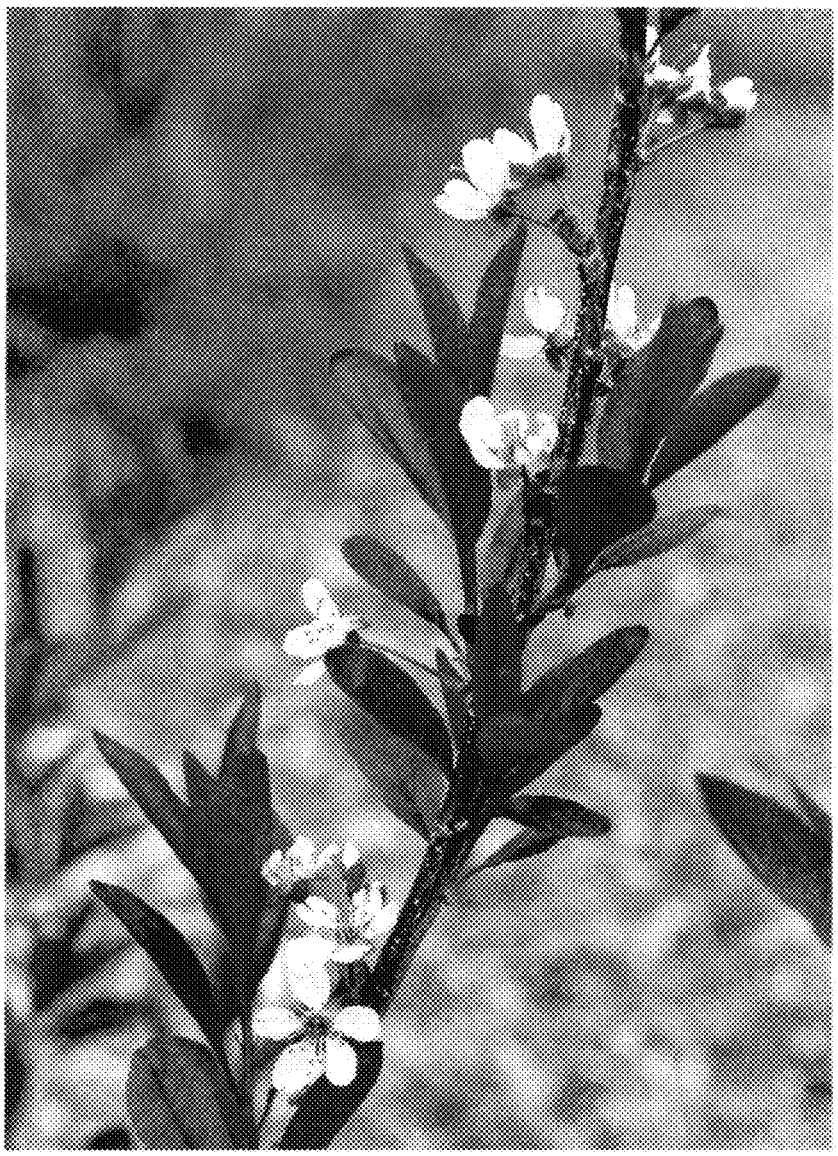

FIG. 2 illustrates in full color a close up of the foliage and flowers.

The plants in FIGS. 1 and 2 are approximately 2.5 years old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'UCONNPCSDR' plants grown in a polyhouse in Grand Haven, Michigan. Plants are approximately 2 years old, in a 3-gallon nursery container. Temperatures ranged from about 5° C. to 10° C. at night and 18° C. to 27° C. during the day. Measurements and numerical values represent averages of typical plant types.

Botanical classification: *Prunus*x*cistena* 'UCONNPCSDR'.

PROPAGATION

Time to produce a rooted young plant: 5 weeks in summer at 18° C. to 27° C., from semi-hardwood cuttings.

Root description: Moderately dense, thin to medium thickness, fleshy and fibrous. Tan to brown in color, not accurately measured with R.H.S. chart.

PLANT

Age of plant described: 2 to 3 years.
Plant type: Perennial shrub.
Growth habit: Upwards and outwards.
Growth rate: Moderate.
Plant vigor: Moderate.
Shape: Compact, low-mounded, spreading.
Height: Approximately 26.7 cm.
Plant spread: Approximately 36.6 cm.
Branching characteristics: Basal; some pinching required to encourage well-rounded habit.
Quantity of lateral branches: 2 to 3 main branches with 3 to 6 branchlets each.
Length of lateral branches: Branch about 25 cm; branchlet about 10 cm.
Diameter of lateral branches: Branch about 6 mm; branchlet about 2 mm.
Stem:
- *Aspect.*—45 to 60°.
- *Shape.*—Rounded.
- *Color.*—New Growth: RHS Purple N77A. Old Growth: RHS Brown 200B.
- *Texture.*—No pubescence observed.
- *Strength.*—Strong.

Internode length: 1 cm.

FOLIAGE

Leaf:
- *Arrangement.*—Alternate, single.
- *Length.*—Approximately 5.5 cm.
- *Width.*—Approximately 2.3 cm.
- *Shape of blade.*—Elliptic.
- *Apex.*—Acute.
- *Base.*—Cuneate.
- *Margin.*—Lightly serrated.
- *Aspect.*—Folded upward at center, flattening with maturity.
- *Texture of top surface.*—Glabrous, smooth.
- *Texture of bottom surface.*—Glabrous, smooth, with pronounced midrib.
- *Pubescence.*—None.
- *Color.*—Young foliage upper side: Near RHS Brown 200A. Young foliage under side: RHS Greyed-Purple N186C. Mature foliage upper side: Near RHS Green NN137B, tinted Greyed-Purple N186C. Mature foliage under side: RHS Greyed-Purple N186C.

Venation:
- *Type.*—Pinnate.
- *Color, upper side.*—RHS Greyed-Purple N187A.
- *Color, under side.*—RHS Greyed-Purple N183C.

Petiole:
- *Length.*—0.9 to 0.13 cm.
- *Width.*—1 mm.
- *Texture.*—Glabrous, all surfaces.
- *Color.*—Upper Surface: RHS Greyed-Purple N187A. Lower Surface: RHS Greyed-Purple N183C.

FLOWER

Flower:
- *Shape/form.*—Single whorl.
- *Habit.*—Single or paired flowers emerging along the length of lateral branches.
- *Flowering season.*—Spring (May).
- *Flower longevity.*—1 week.
- *Fragrance.*—None.
- *Quantity of flowers.*—About 10 per lateral stem.
- *Quantity of buds.*—About 10 per lateral stem.
- *Quantity of flowers and buds.*—50 to 100 per plant.
- *Length.*—1.5 cm.
- *Diameter.*—1.5 cm.
- *Depth.*—0.75 cm.
- *Angle.*—Outwards.
- *Persistence.*—Self-Cleaning.

Bud:
- *Length.*—3 mm.
- *Diameter.*—3 mm.
- *Shape.*—Globose/ovoid.
- *Color.*—RHS Grey-Purple 186C.

Petals:
- *Number.*—6 to 7.
- *Arrangement.*—Single whorl.
- *Length.*—8 mm.
- *Width.*—4 mm.
- *Shape.*—Elliptic.
- *Apex.*—Obtuse.

*Base*.—Cuneate.
*Margin*.—Entire.
*Texture*.—Both surfaces glabrous, soft, and silky.
*Color*.—Immature, upper surface: RHS Red-Purple 69C. Immature, lower surface: RHS Red-Purple 69C. Mature, upper surface: RHS White NN155A. Mature, lower surface: RHS White NN155A.
*Other*.—Petals exhibit a tendency to be somewhat irregularly shaped/folded.

Sepals:
*Number*.—5.
*Arrangement*.—Whorl.
*Appearance*.—Small, rounded, inconspicuous.
*Length*.—2 mm.
*Width*.—1 mm.
*Shape*.—Narrowly elliptic.
*Apex*.—Obtuse.
*Base*.—Fused.
*Margin*.—Entire.
*Texture*.—Both surfaces glabrous.
*Color*.—Upper surface: RHS Greyed-Orange 166A. Lower surface: RHS Greyed-Orange 166A.

Calyx:
*Shape*.—Collar-like, sepals down-curled.
*Length*.—7 mm.
*Width*.—7 mm.

Peduncle:
*Length*.—1.5 cm.
*Width*.—1 mm.
*Color*.—RHS Greyed-Orange 166A.
*Texture*.—Glabrous.
*Angle*.—20° to 45° relative to lateral branch.
*Strength*.—Good, somewhat flexible.

Pedicel: None.

REPRODUCTIVE ORGANS

Gynoecium:
*Pistil number*.—1.
*Pistil length*.—7 mm.
*Stigma shape*.—Rounded.
*Stigma color*.—RHS Greyed-Orange 166C.
*Style length*.—6 mm.
*Style color*.—RHS Greyed-Red 181C.
*Ovary color*.—RHS Greyed-Orange 166A.

Androecium:
*Stamen number*.—10 to 12.
*Filament length*.—5 mm.
*Filament color*.—RHS Red-Purple 69D.
*Anther shape*.—Globose.
*Anther length*.—Less than 1 mm.
*Anther color*.—RHS Greyed-Orange 166B.
*Amount of pollen*.—Sparse.

OTHER CHARACTERISTICS

Fruit/seeds: Not observed.
Disease and pest resistance: Not observed to be susceptible nor resistant to normal diseases and pests of *Prunus cistena*.
Temperature tolerance: Tolerant from −31° C. to 38° C.

What is claimed is:

1. A new and distinct cultivar of *Prunus*x*cistena* plant named 'UCONNPCSDR' as herein illustrated and described.

* * * * *